United States Patent [19]

Krapcho et al.

[11] 4,115,382
[45] Sep. 19, 1978

[54] 3,3-DICHLORO-2-AZETIDINONE DERIVATIVES HAVING BASIC SUBSTITUENTS

[75] Inventors: John Krapcho, Somerset; Chester F. Turk, Kendall Park, both of N.J.

[73] Assignee: E. R. Squibb & Sons, Inc., Princeton, N.J.

[21] Appl. No.: 803,827

[22] Filed: Jun. 6, 1977

[51] Int. Cl.$^2$ .................. C07D 205/08; A61K 31/395
[52] U.S. Cl. ..................... 260/239 A; 260/293.69; 260/326.37; 424/244; 424/267; 424/274; 424/250; 424/248.54; 544/111; 544/359
[58] Field of Search ..................... 260/239 A, 239 AL

[56] References Cited

U.S. PATENT DOCUMENTS

| 3,194,801 | 7/1965 | Perelman | 260/239 A |
| 3,481,920 | 12/1969 | Hargrove | 260/239 A |

OTHER PUBLICATIONS

Duran et al., Tet. Letters 1970, 245-248.
Sekiya et al., Chem. Abs. 84, 163799r (1975).
Sekiya et al., Chem. Abs. 84, 17035x (1976).

Primary Examiner—Donald G. Daus
Assistant Examiner—Mark L. Berch
Attorney, Agent, or Firm—Lawrence S. Levinson; Merle J. Smith; Donald J. Barrack

[57] ABSTRACT

Compounds having the formula

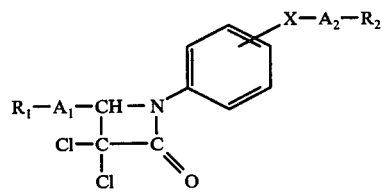

wherein X is oxygen or sulfur; $R_1$ is alkyl, cycloalkyl or aryl; $R_2$ is dialkylamino or a nitrogen containing heterocyclic group; $A_1$ is a saturated bond or an alkylene group having 1 to 4 carbon atoms; and $A_2$ is an alkylene group having 2 to 5 carbon atoms; have antiinflammatory activity.

8 Claims, No Drawings

3,3-DICHLORO-2-AZETIDINONE DERIVATIVES HAVING BASIC SUBSTITUENTS

RELATED APPLICATION

Copending United States patent application Ser. No. 737,864, filed Nov. 1, 1976, now U.S. Pat. No. 4,064,120, issued Dec. 20, 1977, relates to 3,3-dichloro-2-azetidinone derivatives having antiinflammatory activity.

BACKGROUND OF THE INVENTION

Sekiya and Morimoto, Chem. Pharm. Bull., 23, 2353 (1975), disclose that the reaction of trichloroacetic anhydride with Schiff bases yields 3,3-dichloro-2-azetidinones. Exemplary compounds are disclosed, but there is no discussion of any utility for the compounds prepared. Unlike the compounds of Sekiya et al., the compounds of the instant invention contain a basic group making possible the preparation of water-soluble acid-addition salts.

BRIEF DESCRIPTION OF THE INVENTION

Compounds having the formula

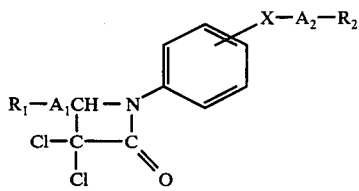   I or a pharmaceutically acceptable salt thereof, have useful antiinflammatory activity. In formula I, and throughout the specification, the symbols are as defined below.

X can be oxygen or sulfur;

$R_1$ can be alkyl, cycloalkyl or aryl;

$R_2$ can be dialkylamino or a nitrogen containing heterocyclic group selected from 1-pyrrolidinyl, 1-piperidinyl, 4-morpholinyl, 1-piperazinyl, and 4-alkyl-1-piperazinyl;

$A_1$ can be a saturated bond or an alkylene group having 1 to 4 carbon atoms; and $A_2$ can be an alkylene group having 2 to 5 carbon atoms.

The term "aryl", as used throughout the specification, whether by itself or as part of a larger group, refers to phenyl or phenyl substituted with a halogen, alkyl, alkoxy, trifluoromethyl, or nitro group.

The terms "alkyl" and "alkoxy", as used throughout the specification, whether by themselves or as part of larger groups, refer to groups having 1 to 6 carbon atoms.

The term "halogen", as used throughout the specification, refers to fluorine, chlorine, bromine or iodine; chlorine and bromine are preferred.

The term "cycloalkyl", as used throughout the specification, refers to groups having 3 to 7 carbon atoms.

The term "alkylene", as used throughout the specification, refers to a straight or branched chain, divalent, saturated hydrocarbon group.

DETAILED DESCRIPTION OF THE INVENTION

The compounds of this invention can be prepared using as starting materials an aldehyde having the formula

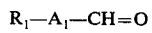   (II)

and a compound having the formula

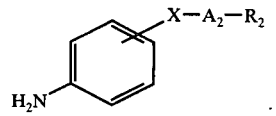   III

Reaction of an aldehyde of formula II with an amine of formula III yields the corresponding Schiff base having the formula

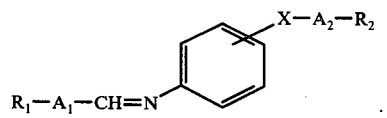   IV

The reaction can be run in an organic solvent, e.g., an aromatic hydrocarbon such as toluene, and will preferably be run at the reflux temperature of the solvent.

Reaction of a Schiff base of formula IV with trichloroacetic anhydride, in accordance with the procedure set forth by Sekiya and Morimoto, Chem. Pharm. Bull., 23, 2353 (1975), yields the corresponding 3,3-dichloro-2-azetidinone of formula I.

The compounds of formula III can be prepared using procedures known in the art; see, for example, U.S. Pat. No. 3,201,401 issued Aug. 17, 1965 and J. Med. Chem., 7, 376 (1964). The compounds are prepared from a compound having the formula

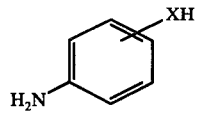   V or a compound having the formula

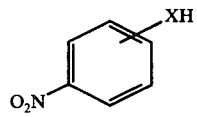   Va

A compound of formula V or Va can be reacted with a compound having the formula

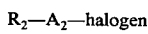   (VI)

to yield the corresponding compound of formula III or the nitro analog. The nitro analog can be reduced to the corresponding amino compound of formula III using procedures well known in the art.

The pharmaceutically acceptable salts of the compounds of formula I are readily prepared using procedures well known in the art. Acid-addition salts are specifically contemplated. Exemplary salts are the hydrohalides, sulfate, nitrate, phosphate, oxalate, tartrate, maleate, citrate, benzenesulfonate, and others.

The compounds of formula I, and the pharmaceutically acceptable salts thereof, can be used for the treatment of inflammation in mammalian species such as mice, dogs, cats, monkeys, etc. Joint tenderness and stiffness (in conditions such as rheumatoid arthritis) are relieved by the compounds of this invention. Formulation of the compounds can be carried out according to accepted pharmaceutical practice in oral dosage forms such as tablets, capsules, elixirs or powders, or in injectable form in a sterile vehicle. The compounds of this invention can be administered in amounts of about 0.1 to 2.0 grams per 70 kilograms of animal body weight per day, preferably about 0.1 to 1.0 grams per 70 kilograms of animal body weight per day.

The following examples are specific embodiments of this invention.

EXAMPLE 1

3,3-Dichloro-1-[2-[3-(dimethylamino)propoxy]phenyl]-4-[3-(trifluoromethyl)phenyl]-2-azetidinone, hydrochloride (1:1)

A.

2-[3-(Dimethylamino)propoxy]-N-[[3-(trifluoromethyl)phenyl]methylene]benzenamine A solution of 19.4g of 2-(3-dimethylaminopropoxy)aniline and 17.4g of m-trifluoromethylbenzaldehyde in 100ml of xylene is refluxed for about 6 hours. The water formed in the reaction is collected in a Dean-Stark tube. The solvent is removed under reduced pressure and the residue fractionated to yield 18.4g of the title compound as an oil, boiling point 155°–160° C. at 0.2–0.3 mm. of Hg.

B.

3,3-Dichloro-1-[2-[3-(dimethylamino)propoxy]phenyl]-4-[3-(trifluoromethyl)phenyl]-2-azetidinone, hydrochloride (1:1)

A solution of 9.0g of 2-[3-(dimethylamino)propoxy]-N-[[3-(trifluoromethyl)phenyl]methylene]benzenamine and 10.8g of trichloroacetic anhydride are reacted in 65 ml of xylene while maintaining the temperature at about 15°–20° C. The solution is slowly heated to 100° C. After heating at about 120°–130° C. for about 30 minutes, the solution is cooled and poured onto ice-water. The mixture is treated with 12g of potassium carbonate and extracted with ether. The gummy ether-insoluble material and aqueous phase are discarded and the ether phase is extracted with a solution of 3 ml of hydrochloric acid in 60 ml of water. This aqueous layer is treated with 6g of potassium carbonate and the liberated base is extracted with four 100 ml portions of ether. The ether phases are combined, dried, treated with Darco and filtered. Evaporation of the filtrate yields 6.9g of oily base. The base (6.3g) is dissolved in dichloromethane, treated with one equivalent of alcoholic hydrogen chloride and the solvents are removed on a rotary evaporator to give a foamy residue which is taken up in 20 ml of acetonitrile. On rubbing, a crystalline solid separates which weighs 1.0g after cooling for about 16 hours (this fraction is believed to be the hydrochloride salt of 2-(3-dimethylaminopropoxy)aniline.

The acetonitrile liquor is evaporated to give 5.8g of a foamy residue which is dissolved in 25 ml of isopropanol and diluted to 100 ml with ether. On seeding (seed crystals are obtained by rubbing a sample of the crude foamy product under ether and cooling for about 16 hours) and rubbing, a crystalline product separates. After cooling for about 16 hours the solid is filtered under nitrogen, washed with ether, and dried in vacuo, yielding 3.8g of material, melting point 157°–160° C. (sintering at 145° C.). Following recrystallization from 15 ml of methanol-90 ml of ether, the product weighs 3.2g, melting point 160°–162° C. (sintering at 150° C.).

EXAMPLE 2

3,3-Dichloro-1-[2-[[3-(dimethylamino)propyl]thio]phenyl]-4-phenyl-2-azetidinone, hydrochloride (1:1)

A.

N-Benzylidene-o-(3-dimethylaminopropylthio)aniline

A mixture of 51g of 2-(3-dimethylaminopropylthio)aniline, 26g of freshly distilled benzaldehyde and 200 ml of xylene is refluxed under an atmosphere of nitrogen. The water formed in the reaction is collected in a Dean-Stark tube; the theoretical quantity is collected after 4 hours of refluxing. The xylene and any unchanged benzaldehyde are removed on the steam bath at 30 mm of Hg, finally at 2 mm of Hg. Fractionation of the residue yields 56g of the title compound, boiling point 182°–189° C. at 0.4 mm of Hg.

B.

3,3-Dichloro-1-[2-[[3-(dimethylamino)propyl]thio]phenyl]4-phenyl-2-azetidinone, hydrochloride (1:1)

Ten grams of N-benzylidene-o-(3-dimethylaminopropylthio)aniline and 14.2g of trichloroacetic anhydride are reacted in 80 ml of xylene as described in Example 1 to give 6.5g of oily base. The base is dissolved in dichloromethane, treated with 3.2 ml of 5.1N alcoholic hydrogen chloride and the solvents evaporated. The foamy residue solidifies when triturated with 30 ml of acetonitrile yielding (after cooling for about 16 hours) 5.0g of material, melting point 166°–168° C. (sintering at 164° C). Crystallization from 25 ml of acetonitrile gives 3.5g of product, melting point 168°–170° C.

EXAMPLES 3–12

Following the procedure of Example 1, but substituting the compound listed in column I for 2-(3-dimethylaminopropoxy)aniline and the compound listed in column II for m-trifluoromethylbenzaldehyde yields the hydrochloride salt of the compound listed in column III.

| Column I | Column II | Column III |
| --- | --- | --- |
| 3) 3-(2-diethylaminoethoxy)aniline | acetaldehyde | 3,3-dichloro-1-[3-[2-(diethylamino)ethoxy]phenyl]-4-methyl-2-azetidinone |
| 4) 4-[4-(1-pyrrolidinyl)butoxy]aniline | n-butyraldehyde | 3,3-dichloro-4-n-propyl-1-[4-[4-(1-pyrrolidinyl)butoxy]phenyl]-2-azetidinone |
| 5) 2-[5-(1-piperidinyl)pentoxy]aniline | valeraldehyde | 4-n-butyl-3,3-dichloro-1-[2-[5-(1-piperidinyl)pentoxy]phenyl]-2-azetidinone |
| 6) 3-[2-(4-morpholinyl)ethoxy]aniline | cyclopropylacetaldehyde | 3,3-dichloro-4-cyclopropylmethyl-1-[3-[2-(4-morpholinyl)ethoxy]phenyl]-2-azetidinone |
| 7) 4-[3-(1-piperazinyl)propoxy]aniline | cycloheptylacetaldehyde | 3,3-dichloro-4-cycloheptylmethyl-1-[4-[3-(1-piperazinyl)propoxy]phenyl]-2-azetidinone |

| | Column I | Column II | Column III |
|---|---|---|---|
| 8) | 2-[4-(4-methyl-1-piperazinyl)butoxy]-aniline | 4-phenylbutyraldehyde | 3,3-dichloro-1-[2-[4-(4-methyl-1-piperazinyl-butoxy]-4-(3-phenylpropyl)-2-azetidinone |
| 9) | 2-[[3-(1-pyrrolidinyl)propyl]thio]-aniline | 5-(2-chlorophenyl)-valeraldehyde | 3,3-dichloro-4-[4-(2-chlorophenyl)butyl]-1-[2-[[3-(1-pyrrolidinyl)propyl]thio]phenyl]-2-azetidinone |
| 10) | 3-[[4-(1-piperidinyl)butyl]thiol]-aniline | (4-methylphenyl)-acetaldehyde | 3,3-dichloro-4-[(4-methylphenyl)methyl]-1-[3-[[4-(1-piperidinyl)butyl]thio]phenyl]-2-azetidinone |
| 11) | 4-[[5-(4-morpholinyl)pentyl]thiol]-aniline | (4-methoxyphenyl)-acetaldehyde | 3,3-dichloro-4-[(4-methoxyphenyl)methyl]-1-[4-[[5-(4-morpholinyl)pentyl]thiol]phenyl]-2-azetidinone |
| 12) | 2-[[2-(1-piperazinyl)ethyl]thio]-aniline | 4-nitrobenzaldehyde | 3,3-dichloro-4-(4-nitrophenyl)-1-[2-[[2-(1-piperazinyl)ethyl]thio]phenyl]-2-azetidinone |

What is claimed is:

1. A compound having the formula

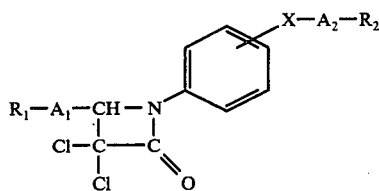

or a pharmaceutically acceptable acid-addition salt thereof, wherein X is oxygen or sulfur; $R_1$ is alkyl, cycloalkyl or aryl; $R_2$ is dialkylamino[, 1-pyrrolidinyl, 1-piperidinyl, 4-morpholinyl, 1-piperazinyl or 4-alkyl-1-piperazinyl]; $A_1$ is a saturated bond or an alkylene group having 1 to 4 carbon atoms; and $A_2$ is an alkylene group having 2 to 5 carbon atoms; wherein aryl is phenyl or phenyl substituted with a halogen, alkyl, alkoxy, trifluoromethyl, or nitro group; alkyl and alkoxy are groups having 1 to 6 carbon atoms; and cycloalkyl is a group having 3 to 7 carbon atoms.

2. A compound in accordance with claim 1 wherein X is oxygen.

3. A compound in accordance with claim 1 wherein X is sulfur.

4. A compound in accordance with claim 1 wherein $R_1$ is alkyl.

5. A compound in accordance with claim 1 wherein $R_1$ is aryl.

6. a compound in accordance with claim 2 wherein $R_1$ is phenyl.

7. The compound in accordance with claim 1, 3,3-dichloro-1-[2-[3-(dimethylamino)propoxy]phenyl]-4-[3-(trifluoromethyl)phenyl]-2-azetidinone, hydrochloride (1:1).

8. The compound in accordance with claim 1, 3,3-dichloro-1-[2-[[3-(dimethylamino)propyl]thio]phenyl]-4-phenyl-2-azetidinone, hydrochloride (1:1).

* * * * *

UNITED STATES PATENT AND TRADEMARK OFFICE
CERTIFICATE OF CORRECTION

PATENT NO. : 4,115,382
DATED : September 19, 1978
INVENTOR(S) : John Krapcho et al It is certified that error appears in the above-identified patent and that said Letters Patent are hereby corrected as shown below:

Column 5, lines 28-31, "[, 1-pyrrolidinyl, 1-piperidinyl, 4-morpholinyl, 1-piperazinyl or 4-alkyl-1-piperazinyl]" should be deleted Signed and Sealed this Twenty-fifth Day of March 1980

[SEAL]

Attest:

SIDNEY A. DIAMOND

Attesting Officer  Commissioner of Patents and Trademarks